United States Patent [19]
Ersek

[11] Patent Number: 5,295,980
[45] Date of Patent: Mar. 22, 1994

[54] MULTI-USE CANNULA SYSTEM

[76] Inventor: Robert A. Ersek, 62 Pascal, Austin, Tex. 78705

[21] Appl. No.: 768,010

[22] Filed: Sep. 30, 1991

Related U.S. Application Data

[63] Continuation-in-part of Ser. No. 428,605, Oct. 30, 1989, abandoned.

[51] Int. Cl.5 .............................................. A61M 5/32
[52] U.S. Cl. ...................................... 604/272; 606/171
[58] Field of Search ................ 604/272, 170; 606/171

[56] References Cited

U.S. PATENT DOCUMENTS

| | | | |
|---|---|---|---|
| 2,555,493 | 6/1951 | Kirschbaum | 606/264 |
| 3,937,222 | 2/1976 | Banko | 606/170 |
| 4,200,106 | 4/1980 | Douvas et al. | 606/170 |
| 4,490,139 | 12/1984 | Huizenga et al. | 604/272 |
| 4,815,462 | 3/1989 | Clark | 606/170 |
| 4,819,635 | 4/1989 | Shapiro | 606/170 |
| 4,850,354 | 7/1989 | McGurk-Burleson et al. | 606/74 |
| 4,850,373 | 7/1989 | Zatloukal et al. | 604/264 |
| 4,959,049 | 9/1990 | Smirmaul | 606/161 |
| 5,061,238 | 11/1991 | Shuler | 606/170 |
| 5,084,052 | 1/1992 | Jacobs | 606/170 |

FOREIGN PATENT DOCUMENTS 0466002  5/1937  United Kingdom ............... 604/272

Primary Examiner—Edgar S. Burr
Assistant Examiner—Anthony H. Nguyen
Attorney, Agent, or Firm—Haugen and Nikolai

[57] ABSTRACT

A universal infusion/aspiration cannula system includes a generally rounded tubular cannula member having a conduit or tubular portion provided with a rounded, partially, open, blunt insertion tip and a proximal end adaptable to standard fittings. The cannula alone allows for the blunt atraumatic dissection through intervening tissues and upon withdrawal, the simultaneous infusion of space filling substances, living tissues or hemostatic agents. A stilette member is provided which is operable within the cannula and the external dimensions of which approximate the internal dimensions of the cannula member wherein the stilette can be rotated or advanced and retracted as a saw to either amputate, cut or saw and grasp a biopsy specimen.

4 Claims, 4 Drawing Sheets

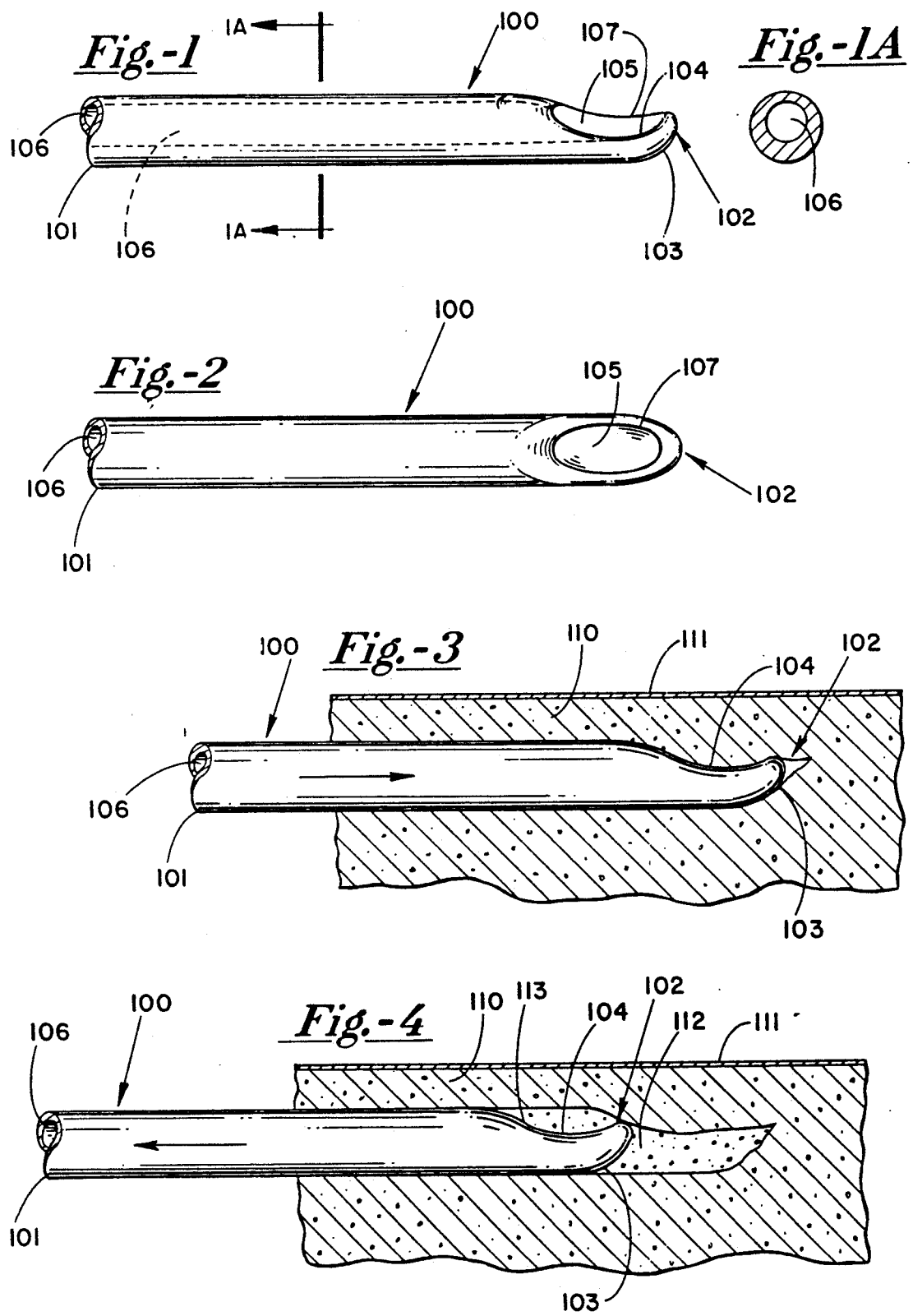

MULTI-USE CANNULA SYSTEM

CROSS-REFERENCE TO RELATED APPLICATION

This application is a continuation-in-part of application Ser. No. 07/428,605, filed Oct. 30, 1989, now abandoned.

BACKGROUND OF THE INVENTION

Field of the Invention

The present invention relates generally to surgical cannula or needle devices which may be used in conjunction with slender cutting devices or stilettes in subcutaneous medical procedures including the dissection, injection, aspiration, and biopsy. More particularly, the present invention relates to an improved cannula device or cannula/stilette combination which allows for all of these procedures to be achieved atraumatically using the same device.

Discussion of the Related Art

Historically, each of the above-mentioned procedures has been done with a different needle, cannula, tube/cannula, or cannula/stilette combination and technology concerning each has, to a great extent, developed separately. In order that a more comprehensive understanding of the present invention can be achieved, some background discussion with regard to the various procedures and approaches and devices used is in order.

There are four general categories of procedures where such devices are used:

(1) the surgical dissection of tissues and organs;
(2) injections, which, as used in this application, means the micro-implantation of substances for hemostasis (clotting), transplantation as of autologous fat, prosthetic placement of substances as in collagen injections, silicone injections, or fibril or other biocompatible substances;
(3) aspiration or removal of substances which, for example, refers to the removal of subcutaneous fat for which the best example is liposuction where the primary goal is the removal of fat tissue to restore form or function . . . where a proliferation of subcutaneous fat distorts the body shape; and
(4) biopsy which involves the retrieval of intact sample portions of representative tissue from a specific area of the body or organ for examination under a microscope.

Traditionally, surgical dissection has been accomplished by a variety of instruments. Dissection in combination with aspiration has generally been accomplished by the use of blunt dissection tubes in the form of round-tipped rods which have enabled plastic surgeons to remove large amounts of subcutaneous fat safely with little trauma. These instruments have in common that they are small in size (normally less than one centimeter in diameter) and have a rounded blunt tip. These attributes make it possible to pass such devices through the subcutaneous plane and through muscle and through many other types of tissue without injuring the noble structures of such tissues as arteries, veins, nerves or tendons. The rounded blunt end enables bodily structures which are filamentous and stronger than the surrounding fat or muscle to be easily pushed aside by the gently curved blunt end leaving such tissue generally intact.

Thus, with the blunt method of suction lipectomy, wide areas of the body, i.e., the entire abdomen, thighs, and hips, can be treated by multiple radial passages of such cannulae. As long as the cannula is advanced only to and fro and never side to side, noble tissue structures penetrated are left intact and recovery may be complete even though vast amounts of subcutaneous tissue be removed. Such procedures are described in greater detail by the inventor and others in Ersek, R. A., et al., "Suction Lipectomy: A Useful New Tool for the Plastic Surgeon," Texas Medicine, Vol. 83, March 1987; Ersek, et al., "Suction Assisted Lipectomy for Correction of 202 Figure Faults in 101 Patients: Indications, Limitations, and Applications," Plastic and Reconstructive Surgery, November 1986; and Robert A. Ersek, M.D., "Suction Assisted Lipectomy—The Blunt Technique," Travis County Medical Journal, May 1984.

Cannulae and other needle devices utilized for aspiration have generally been designed with a blunt tip but with one or more side holes, possibly near the tip for aspirating the actual tissue to be removed. Much experimentation has been done with regard to the shape, location and size of the aspiration holes but, to date, all have suffered from certain drawbacks. Although some of these devices have been designed with holes near the tip, none has combined a blunted rounded dissecting tip and blunted rounded side hole.

Injections, of course, take different forms. With respect to medical injections, a sharp needle is usually employed because the trauma of a sharp needle is inconsequential compared to the injection of a bolus of medication. With the injection of semi-solid material of a class including silicone particles, dense collagen, fibril or the subsequent reinjection of aspirated fat at other than the removal site, an atraumatic dissection, as described above followed by injection with a blunt tipped device is certainly the preferred procedure.

A variety of injection cannula tips has been developed that have a rounded tip at the end and a side hole. If many paths are first formed at the site, it is possible to inject fat or other substances through a side hole device. However, if the injection site is other than normal tissue, problems may arise. When the injection site involves scar tissue or partially scarred tissue, such as occurs in areas which have been over-treated by liposuction, then the passage of a blunt cannula instrument through this more dense tissue is more difficult. The simultaneous concurrent injection of material through a side hole of existing cannulae does not occur because the diameter of the hole through dense, more fibrous tissue is approximately the same as the dissecting blunt cannula leaving no space for the material to be injected. If a sharp bevelled-tip needle be used, the goal of atraumatic injection is defeated and far more bleeding occurs at the site and the success of the fat grafts or other semi-solid injecting is seriously imperiled. Square-tipped open tubes have also been used, but with the devices, passage through living tissue of any kind is extremely difficult especially in the case of dense scar tissue.

All of the previous designs, variously placed and shaped aspiration holes generally function well for aspiration. None has been designed, however, that also functions successfully for atraumatic dissection and injection as described herein. Generally, it may be concluded that injection of semi-solid substances of a class including autologous fat, silicone particles, dense collagen or fibril is very difficult and indeed impossible through prior art cannulae.

The procedure of biopsy is an extremely important diagnostic tool. Many tools have been used to effect the remote procurement of small segments of target organs or tissue for examination under the microscope. They include a wide variety of cutting and retrieving needles, cannulae, forceps and other devices which presently find daily use as biopsy instruments. In general, these are sharp cutting needles. Some have a blunted thin cutting or stilette member to allow atraumatic passage through the intervening tissues to the target organ, such as the liver. Still other biopsy needle systems are provided with a needle member together with a separate stilette or cutting member. However, none presently combines all the attributes, including atraumatic passage of the cannula member, for precise placement in the sample site desired, precise application of negative pressure to secure the target tissue within the lumen of the device, precise cutting and retrieval of the desired tissue sample specimen. In addition, the atraumatic subsequent injection of hemostatic agents to fill the space occupied by the biopsy specimen is desirable to thereby create a pressure producing, clot inducing plug to minimize bleeding. Post-biopsy bleeding is of such a threat with prior art biopsy devices that simple needle biopsy procedures often indicate one or two days hospitalization just for observation in case excess bleeding should occur.

SUMMARY OF THE INVENTION

The present invention provides an universal cannula which combines the attributes desired for a variety of procedures. The invention contemplates safe atraumatic subcutaneous passage which allows the gentle dissection of bodily tissues, the injection through the same device of medications, implantations, hemostatic biopsy replacement devices and further provides an atraumatic means for the aspiration of subcutaneous fat and other tissues including safe biopsy retrieval with subsequent implantation of hemostatic agents to minimize the dangers and trauma of biopsy.

The universally applicable device of the invention combines an uniquely shaped cannula member with an uniquely shaped cutting stilette member. In its preferred form, the cannula member has a rounded and blunted tip end of reduced cross-section containing a side discharge/intake opening and a tubular member connecting the end opposite from the tip adapted to a current variety of well-known standard fittings, such as tapered tubing fittings, and other fittings that will occur to those skilled in the art. The stilette has a cutting or blade tip that resides inside the hollow lumen of the cannula member and upon rotation effects the closure of the opening of the cannula and the cutting of any intervening tissue. A barbed pointed end may be provided to aid in grasping said tissue. The stilette is further provided with a shaft member that connects to a grippable opposite end that extends through the cannula tube.

The system operates through an incision in the skin usually made with a similar sized blade or similar sized needle and the cannula is then passed through this incision. The semi-rounded, semi-blunted cannula end will atraumatically plow through the subcutaneous fat pushing aside amorphous fat and preserving other nobel elements encountered at the site or treatment where the process of interest is performed as described more fully elsewhere.

BRIEF DESCRIPTION OF THE DRAWINGS

In the drawings:

FIG. 1 is a side elevation of a view depicting a typical cannula tube in accordance with the invention;

FIG. 1A is a sectional view taken along line A—A of FIG. 1;

FIG. 2 shows a top view of the cannula tube of FIG. 1 as rotated 90 degrees toward the viewer;

FIG. 3 is a partial sectional view of the cannula inserted in a subcutaneous environment;

FIG. 4, also partly in section, shows the cannula of FIG. 3 partially retracted from the subcutaneous position of FIG. 3;

DESCRIPTION OF THE PREFERRED EMBODIMENTS

Figure 5:
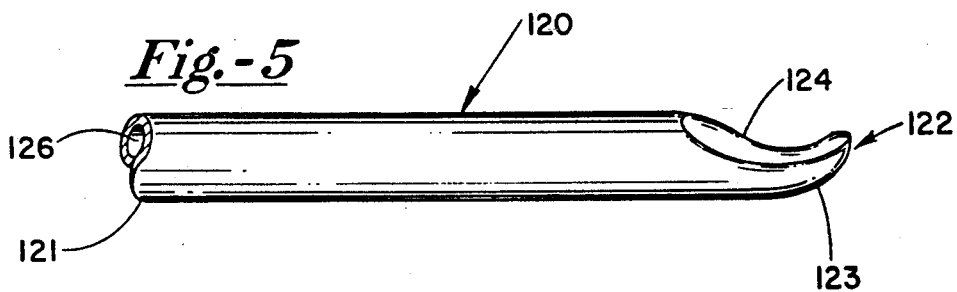
FIG. 5 depicts an alternate embodiment of the cannula in FIG. 1.

FIGS. 1 and 2 show side elevation and top views of a typical cannula member in accordance with the invention. The cannula member is generally depicted at 100 including a distal fitting end 101 and a blunt tip 102. The tip has a rounded, blunt closed penetrating end portion 103 and a gently tapered rounded portion 104 with opening 105 (FIG. 2) that communicates with the generally hollow interior 106. As better depicted in the sectional view of FIG. 1A, the hollow interior 106 of the member 100 is preferably somewhat axially asymmetric with respect to the member 100. The opening 105 nominally takes up about one-half the area of the recessed portion 104. The outer edge 107 of the opening 105 is preferably designed to be blunt and non-evasive to surrounding tissue but with an inner edge component that cooperates with the cutting surface of a compatible stilette member to produce precise excision and sealing of the opening during biopsy.

FIG. 3 depicts a side view of the cannula 100 as it might be seen tunneling through subcutaneous tissue 110 beneath the skin 111 thereby creating a channel (as better illustrated at 112 in FIG. 4) by the gentle plowing of its blunted, tapered tip member 102. FIG. 4 illustrates the cannula as partially retracted from further penetration and illustrates the injection of a biocompatible substance at 113 such as collagen, autologous fat, silicone, permanent injectable microimplants consisting of micro particles dispersed in a compatible physiological vehicle, or other material which may be exuded from the opening 105 under controlled pressure.

From the foregoing, it will further be appreciated that an important consideration with respect to the cannula of the invention, generally, is that it is decidedly a blunt instrument designed to improve atraumatic subcutaneous tissue intrusion. A further important consideration involves the distal opening or hole which is located near the distal end of the cannula portion and connects with the internal lumen. With respect to the distal opening, it is important that the opening be located on the taper between the blunt distal end and the substantially cylindrical shaft portion of the device but that the opening encompass neither the distal end nor any portion of the shaft.

Figure 10A:
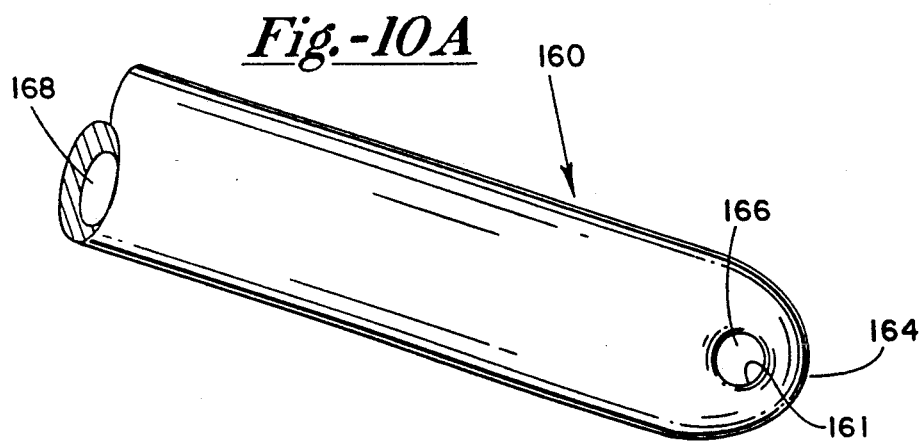
FIG. 10A is a fragmentary view from above the distal opening of another embodiment of the cannula of the invention.
Figure 10B:
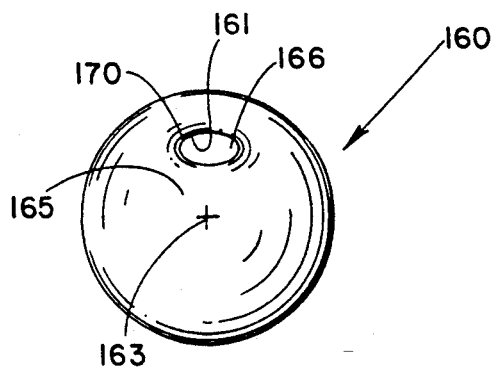
FIGS. 10B and 10C represent a greatly enlarged end and fragmentary side view of the embodiment of FIG. 10A.
Figure 10C:
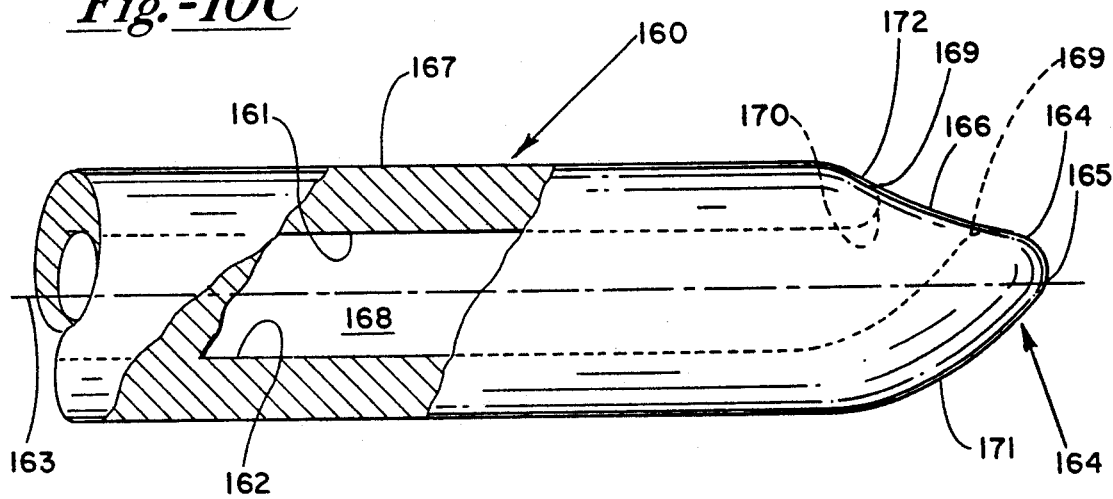

This aspect of the preferred arrangement for the distal end of the device is best illustrated by FIG. 10A and the greatly enlarged views of FIGS. 10B and 10C in which a fragmentary distal section of a cannula is shown at 160. Broken lines 161 and 162 describe the hollow internal lumen of the cannula, the centerline of which is depicted by 163. The center of the relatively snub-nosed blunt end 164 is depicted by 165. The distal opening is shown at 166 and is located beginning at a point above the center of the nose 165 and ending at a point below the cylindrical shaft of the device depicted by 167. It is important to note that there are no sharp edges with respect to the cannula system of the invention. Thus, the entry to the opening 166 which connects to the internal lumen 168 is not a square-cornered hole as one would obtain by drilling straight through the thickness of the cannula; but, instead, the edges of the hole as at 169 and 170 in FIG. 10C are connected by a rounded or curved transition. It should further be noted that the bottom nose contour 171 is generally an outwardly directed arcuate shape or positive curve, and the upper nose contour 172 is generally an inwardly directed arcuate or curved shape or recess. These blend together to form the taper connecting the blunt end 164 with the generally cylindrical shaft 167 and also involve only gently rounded corners rather than any squared or sharp edges. Because the edges of the hole or opening 166 are rounded and have rounded corners, tissue encountered in the subcutaneous invasion of the device tends to be gently pushed aside by the blunt nose, slide over these rounded corners and not be damaged by or enter the opening 166. Tissue encountered is not "center punched" as occurs with other cutting and biting devices where the opening is more directly in the nose of the cannula. In addition, it is decidedly easier to inject material from the opening 166 than from openings on the side or shaft portion of the side discharging/aspirating cannula. It is believed that FIGS. 10A, 10B and 10C portray or illustrate the atraumatic or benign nature of the subcutaneous tissue penetrating cannula device of the invention.

FIG. 5 is a side elevational view of a cannula member 120 which is similar to that of FIGS. 1-4 having a distal fitting end 121, blunt tip 122, rounded blunt closed portion 123, and tapered, rounded portion having an opening at 124. The arcuate shape of the cannula 120 is designed to be compatible with and complementary to the arcuate shape of a stilette member or biopsy blade, described below. The cannula 120 also has an asymmetric, generally hollow interior as at 126.

Figure 6:
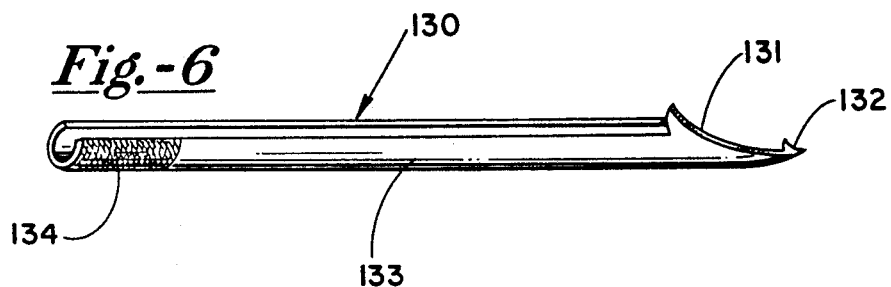
FIG. 6 depicts a stilette member for use in conjunction with the cannula of FIG. 5.

A biopsy blade or stilette is shown generally at 130 in FIG. 6. The stilette has a generally arcuate cutting edge 131 which includes an outer tip member having a tip barb 132. A shaft member 133 having a grippable proximal end 134 is utilized to operate the cutting member both in an axial and rotational manner.

Figure 7:
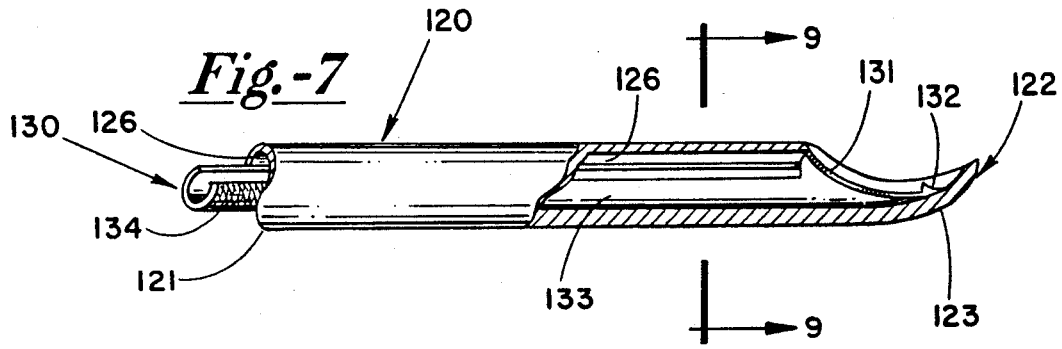
FIG. 7 depicts, with parts cut away, the stilette of FIG. 6 as inserted and cooperating with the cannula tube of FIG. 5.

As is better shown in FIG. 7, the arcuate shape of the cutting member 131 is of the general size and configuration of the tapered open portion of the cannula 124 and the shaft member 134 is of a size to be compatibly accommodated within the tubular hollow 126 of the cannula 120. It is shown nesting in the opening position so that the blade portion 131 essentially coincides with the edge of the opened cannula tip with only the small barb member 132 protruding from the tip portion.

Figure 8:
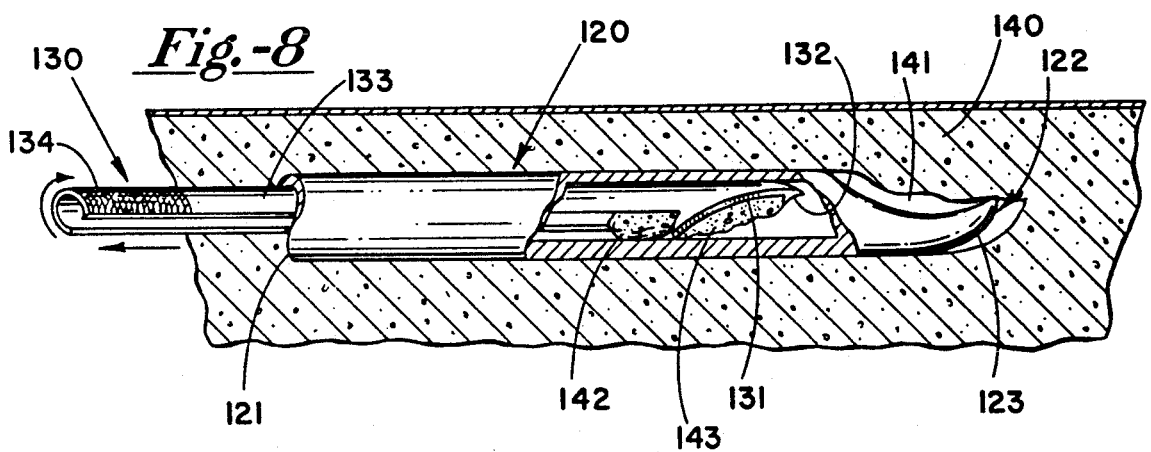
FIG. 8 is a partial sectional view, with parts cut away, of the cannula/stilette system of FIG. 7 in a subcutaneous insertion position at the start of a retraction.

FIG. 8 is an additional enlarged partial sectional side elevational view, with parts cut away, of the cannula, in situ within the subcutaneous tissue 140 in which the stilette member has been partially retracted and rotated about 180 degrees from the position depicted in FIG. 7. In this illustration, a biopsy has already been taken from the advancing wall of the channel at 141 and is seen as a tissue fragment 143 which has been cut and trapped behind the barb 132 of the arcuate cutting member 131. A fragment is also shown behind the cutting member 131 at 142.

Figure 9:
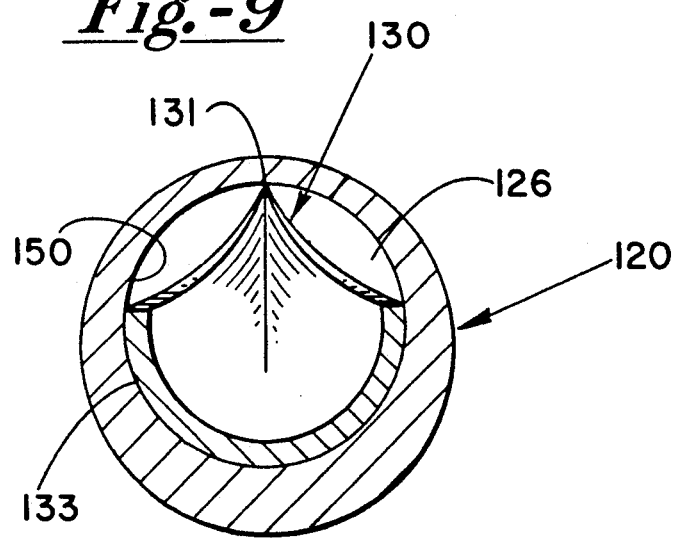
FIG. 9 is a sectional view taken along line 9—9 of FIG. 7.

A further detail of the combination of the stilette/cannula combination of FIG. 7 is seen in the enlarged cross-sectional view of FIG. 9. This Figure again illustrates the cooperation of the system parts. The outer cannula member 120 is down with an asymmetric bore 126. The shaft member 134 of the stilette is shown juxtaposed in the inner wall 150 of the cannula 120.

Generally, procedures utilizing the cannula or the cannula/stilette combination of the invention involve first making a small incision through the skin as proximate as convenient to the site of interest, usually with a similar size blade or similar size needle as that to be inserted, and thereafter passing the cannula through the incision. As guided to the site, the semi-rounded, semi-blunted cannula atraumatically plows its way through the subcutaneous tissue pushing aside the amorphous fat and preserving the noble integrity of muscle and other tissue. If, for example, the lumen or tube of the cannula be filled with an injectable substance such as collagen, silicone, other bio-compatible plastic material particles or other semi-solid or semi-fluid substances, little or no foreign material in the form of fat or other tissue will enter the lumen because of the shape of the ends of the rounded hole that comprises the open portion of the tip member. This reduces problems associated with transporting foreign or extraneous material from one site and depositing it at another where an infection may develop. The cannula can proceed to the precise site of injection where the contained material can be exuded into the tissue substantially in its pure form.

If the device be used for aspiration of subcutaneous fat, then, after proceeding to the site of aspiration or removal in the manner above, a negative pressure of vacuum is applied to the hollow interior of the cannula in a well-known manner using compatible connecting devices familiar to those skilled in the art such that continuous retrieval and removal of fat or other tissue through the cannula can take place as the cannula is passed to and fro repeatedly through the tissue. This is generally the case where the amount of subcutaneous fat is being reduced over a large bodily area. Normally, infusion, injection, or implantation sites require more exacting location and are decidedly more local. The connecting devices and their use, however, are well known. As illustrated in FIG. 8, for example, injection or implantation is more readily accomplished utilizing a retraction or backward movement of the cannula in the channel formed in the insertion mode so that the implantation material can flow from the distal opening in the taper of the tip member to fill the cavity created by the insertion mode.

When the system is used as a biopsy device, the stilette member is rotated 180 degrees within the lumen such that the open portion of the tip member is covered by the slightly recessed sharp edged portion of the blade member. The remaining portion of the blade member then, because it is shaped like a segment of the cylinder similar to the inside dimensions of the tip portion of the cannula, closes the opening in the cannula so that intervening tissue will neither be injured nor entrapped to provide an unreliable sample. Once the cannula guides the stilette device to the area of interest within the target organ for biopsy, the blade member is then rotated again 180 degrees with the application of a negative pressure of vacuum in the cannula lumen portion. This negative pressure then sucks tissue into the hollow section while at the same time, rotation of the blade allows for the precise amputation of a portion of the tissue of interest having the proximate diameter of the cannula a length of the blade member. The barb member at the tip of the blade offers the positive entrapment of the biopsy specimen as the blade and shaft members of the stilette member are retrieved from the cannula.

The exact size of the sample, of course, will vary with the size of the stilette member and also with the density of the tissue being biopsied. Almost any kind of tissue including muscle, fat, kidney, liver, etc. may be sampled in this manner. It has been found that relatively soft tissue, such as liver, may be aspirated by the negative pressure and rather large portions whereas hard tissue such as bone will be aspirated very little in the biopsy segment turns out to be little more than a scraping in that situation. Cartilage, muscle and other semi-dense tissues will enter the lumen to a more or less degree depending on their viscosity and density. Upon removal of the biopsy by the stilette member through the hollow tubular interior of the cannula, well-known expanded hemostatic agents such as lyophilized porcine dermal collagen or body putty made with microfibular collagen and a patient's blood, minced autologous muscle or other potentially hemostatic agents are then injected precisely into the biopsy site to prevent subsequent bleeding. Silicone and other polymers may also be used where appropriate in a well-known manner.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A surgical combination infusion/aspiration cannula comprising an elongated probe member characterized by:

(a) a single tubular distal section having a generally cylindrical, axially asymmetrical, hollow interior bore, the asymmetry producing relatively thick and relatively thin sidewall sectors, the interior bore configured to optionally carry a stilette member therein;
    (b) an insertion tip distally contiguous with the tubular section and of asymmetrically reduced outer cross-section with respect to the tubular section;
    (c) a transition portion in the form of a gradual arcuate taper, the taper being generally in the relatively thin wall sector of the tubular section;
    (d) the tip portion further comprising a rounded blunt closed tissue penetration end for atraumatically penetrating subcutaneous tissue and having a generally radially disposed infusion/aspiration opening rearward of the penetration end, the opening being configured with the asymmetry of cross-section so as to be at least partially protected to prevent incursion of foreign material during insertion of the probe; and
    (e) wherein the edges of the opening have a blunt outward directed surface and sharpened inner edge component configured to cooperate with the cutting surface of a compatible stilette member to excise tissue specimens.

2. The apparatus of claim 1 wherein the proximal end of the tubular section is adapted to connect to both injection and aspiration devices.

3. A combination infusion/aspiration cannula comprising an elongated probe member characterized by:

(a) a generally cylindrical tubular shaft section having a hollow interior lumen;
    (b) an insertion tip section at the distal end of the tubular shaft section comprising a relatively blunt, snub-nosed, but gradually curved, tissue penetrating distal tip section having a closed distal tip end of greatly reduced outer cross-section with respect to the cylindrical tubular shaft section for atraumatically penetrating subcutaneous tissue;
    (c) a transition portion of the cannula between the tubular shaft and the snub-nosed tip describing a slightly convex lower taper shape and a slightly concave recessed upper taper curve shape;
    (d) an angularly disposed infusion/aspiration port opening accessing the distal end of the interior lumen in the upper shape of the transition section proximal of the closed snub-nosed tip and distal of the cylindrical shaft, the opening being contained within the tapered cross-sectional area and directed at an acute angle with the axis of the cylindrical tubular shaft of the cannula;
    (e) wherein the edge of the infusion/aspiration port opening is itself further characterized by a dull, curved transition surface; and
    (f) wherein the diameter of the infusion/aspiration port opening is less than half of the external diameter of the cannula.

4. The apparatus of claim 3 wherein the infusion/aspiration port opening is generally circular.

* * * * *